(12) United States Patent
Lavallee et al.

(10) Patent No.: US 9,795,319 B2
(45) Date of Patent: Oct. 24, 2017

(54) METHOD AND DEVICE FOR NAVIGATION OF A SURGICAL TOOL

(71) Applicant: IMACTIS, La Tronche (FR)

(72) Inventors: Stephane Lavallee, Saint Martin d'uriage (FR); Lionel Carrat, Saint Martin d'here (FR)

(73) Assignee: IMACTIS, La Tronche (FR)

( * ) Notice: Subject to any disclaimer, the term of this patent is extended or adjusted under 35 U.S.C. 154(b) by 245 days.

(21) Appl. No.: 14/078,279

(22) Filed: Nov. 12, 2013

(65) Prior Publication Data

US 2014/0073914 A1 Mar. 13, 2014

Related U.S. Application Data

(63) Continuation of application No. 13/146,206, filed as application No. PCT/EP2010/050999 on Jan. 28, 2010, now Pat. No. 8,611,985.

(60) Provisional application No. 61/148,122, filed on Jan. 29, 2009.

(51) Int. Cl.
| | | |
|---|---|---|
| *A61B 5/06* | (2006.01) | |
| *A61B 6/03* | (2006.01) | |
| *A61B 17/34* | (2006.01) | |
| *A61B 17/00* | (2006.01) | |
| *A61B 90/00* | (2016.01) | |
| *A61B 34/20* | (2016.01) | |

(52) U.S. Cl.
CPC ............... *A61B 5/062* (2013.01); *A61B 6/03* (2013.01); *A61B 17/00234* (2013.01); *A61B 17/3478* (2013.01); *A61B 34/20* (2016.02); *A61B 90/39* (2016.02); *A61B 2017/00699* (2013.01); *A61B 2034/2046* (2016.02); *A61B 2034/2051* (2016.02); *A61B 2090/3983* (2016.02); *A61B 2090/3995* (2016.02)

(58) Field of Classification Search
CPC .......... A61B 17/00234; A61B 17/3478; A61B 19/5244; A61B 19/54; A61B 2017/00699; A61B 2019/5246; A61B 2019/5251; A61B 2019/5483; A61B 2019/5495; A61B 5/062; A61B 6/03
See application file for complete search history.

(56) References Cited

U.S. PATENT DOCUMENTS

| | | |
|---|---|---|
| 5,995,862 A | 11/1999 | Gallorini |
| 6,203,543 B1 | 3/2001 | Glossop |
| 6,546,279 B1 | 4/2003 | Bova et al. |

(Continued)

FOREIGN PATENT DOCUMENTS

| | | |
|---|---|---|
| CA | 2295782 | 1/1999 |
| CA | 2275047 | 12/2000 |

(Continued)

OTHER PUBLICATIONS

Van der Eisen, et al., "Marker-guided multimodality matching of the brain", European Radiology, vol. 4, 1994, pp. 45-51.*

(Continued)

*Primary Examiner* — Katherine Fernandez
(74) *Attorney, Agent, or Firm* — Blakely Sokoloff Taylor & Zafman LLP

(57) ABSTRACT

The invention relates to a method of navigation of a tool to be used in a surgical operation for treating a target region within the body of a patient.

5 Claims, 9 Drawing Sheets

(56) References Cited

U.S. PATENT DOCUMENTS

| | | |
|---|---|---|
| 2002/0183608 A1 | 12/2002 | Marmulla et al. |
| 2003/0000535 A1 | 1/2003 | Galloway, Jr. et al. |
| 2003/0135115 A1* | 7/2003 | Burdette .................. A61B 8/12 600/437 |
| 2003/0179856 A1 | 9/2003 | Mitschke et al. |
| 2004/0097952 A1 | 5/2004 | Sarin et al. |
| 2005/0075563 A1 | 4/2005 | Sukovic et al. |
| 2005/0096536 A1 | 5/2005 | Peterson |
| 2005/0182319 A1 | 8/2005 | Glossop |
| 2006/0095066 A1 | 5/2006 | Chang et al. |
| 2006/0122497 A1 | 6/2006 | Glossop |
| 2007/0238978 A1 | 10/2007 | Kumar et al. |
| 2008/0045972 A1 | 2/2008 | Wagner et al. |
| 2008/0064947 A1 | 3/2008 | Heruth et al. |
| 2008/0221520 A1* | 9/2008 | Nagel .................. A61B 90/36 604/116 |
| 2008/0285707 A1 | 11/2008 | Kalender et al. |
| 2008/0300478 A1 | 12/2008 | Zuhars et al. |
| 2010/0174192 A1* | 7/2010 | Azuma .................. A61B 6/5247 600/443 |

FOREIGN PATENT DOCUMENTS

| | | |
|---|---|---|
| CA | 2377418 | 9/2002 |
| CA | 2483718 | 3/2005 |
| CA | 2586560 | 6/2006 |
| CA | 2612603 | 12/2006 |
| CA | 2620196 | 3/2007 |
| DE | 199 08 903 | 9/2000 |
| DE | 199 63 440 | 7/2001 |
| DE | 100 45 376 | 4/2002 |
| DE | 10 2005 044 033 | 3/2007 |
| DE | 10 2005 051 102 | 4/2007 |
| DE | 10 2006 026 913 | 4/2007 |
| DE | 10 2006 037 604 | 2/2008 |
| WO | 02/00130 | 1/2002 |
| WO | 02/061371 | 8/2002 |
| WO | 2005/013841 | 2/2005 |
| WO | 2007/002079 | 1/2007 |
| WO | 2007/113815 | 10/2007 |
| WO | 2008/017469 | 2/2008 |
| WO | 2008/065600 | 6/2008 |
| WO | 2008/130355 | 10/2008 |
| WO | 2008130355 | 10/2008 |
| WO | 2008/142629 | 11/2008 |
| WO | 2008142629 | 11/2008 |
| WO | WO/2008/149573 | * 11/2008 |

OTHER PUBLICATIONS

Int'l Search Report for PCT/EP2010/050999, mail dated Jun. 29, 2010.

Yaniv et al.; "Needle-Based Interventions With the Image-Guided Surgery Toolkit (IGSTK): From Phantoms to Clinical Trials"; IEEE Transactions on Biomedical Engineering.; Apr. 2010; vol. 52; No. 4; pp. 922-933.

F. Kinoshita, et al.; "CT-Guided Transthoracic Needle Biopsy Using a Puncture Site-Down Positioning Technique"; Am. J. Roentgenol.; 2006; vol. 187; No. 4, pp. 926-932; American Roentgen Ray Society.

Gevenois et al.; "CT-Guided Percutaneous Drainage of an Anterior Mediastinal Abscess With a 16 F Catheter"; Eur Respir J; 195; vol. 8, pp. 869-870; ERS Journals Ltd.

L. Thanos et al.; "Image-Guided Radiofrequency Ablation of a Pancreatic Tumor With a New Triple Spiral-Shaped Electrode"; Cardiovasc Intervent Radiol; 2010; vol. 33, pp. 215-218; Springer.

Nagel et al.; "A Navigation System for Minimally Invasive CT-Guided Interventions Med Image Comput Comput Assist Inter Int Conf"; Med Image Comput Comput Assist Interv.; 2005; vol. 8; Pt. 2; pp. 33-40; Springer-Verlag Berlin Heidelberg.

M. Das et al.; "Augmented Reality Visualization for CT-Guided Interventions: System Description, Feasibility, and Initial Evaluation in an Abdominal Phantom"; Radiology; Jul. 2006; vol. 240; No. 1; pp. 230-235; RSNA.

Wallace et al.; "Out-of-Plane Computed-Tomography-Guided Biopsy Using a Magnetic-Field-Based Navigation System"; Cardiovasc Intervent Radiol.; 2006; vol. 29, pp. 108-113; Springer Science+Business Media, Inc.

* cited by examiner

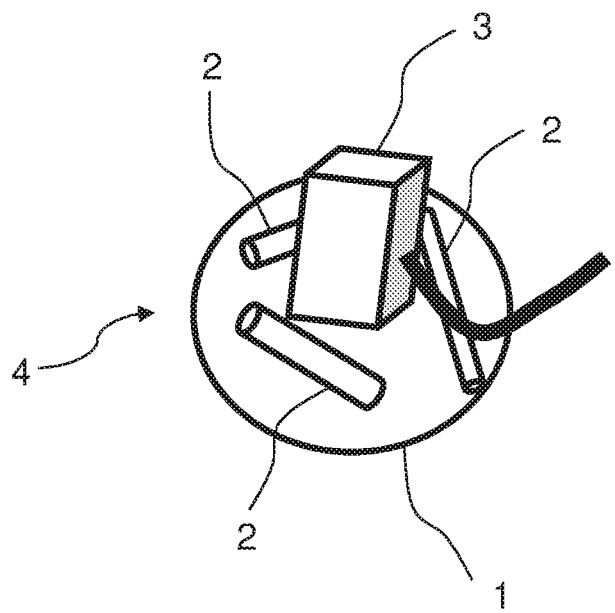
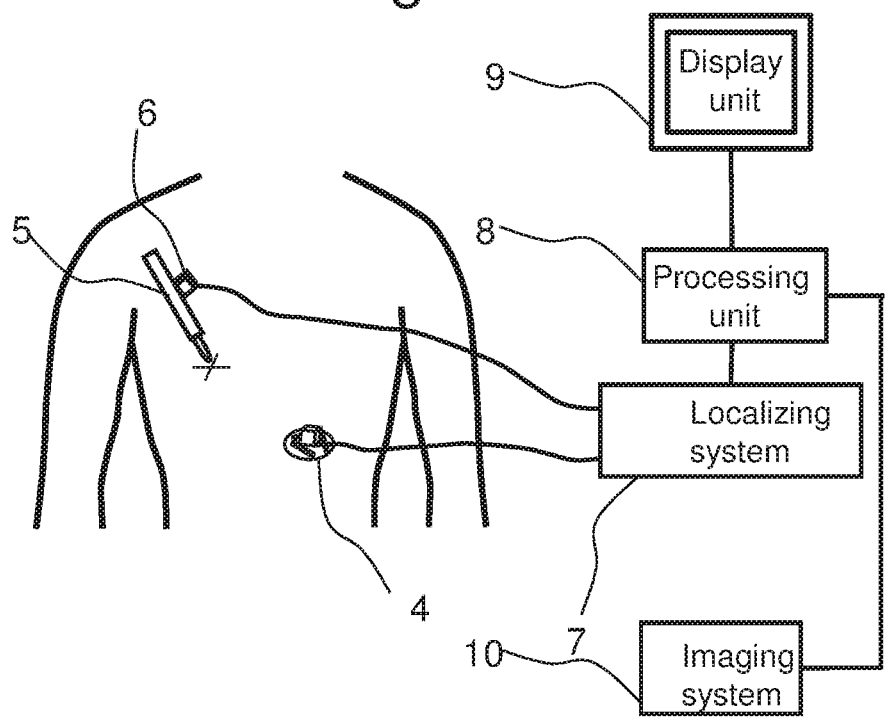

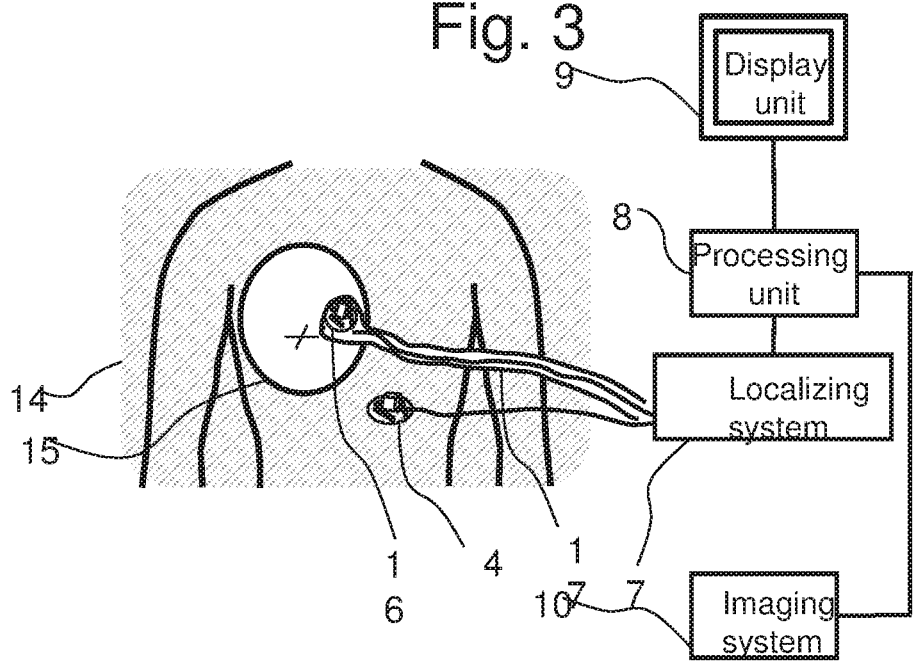
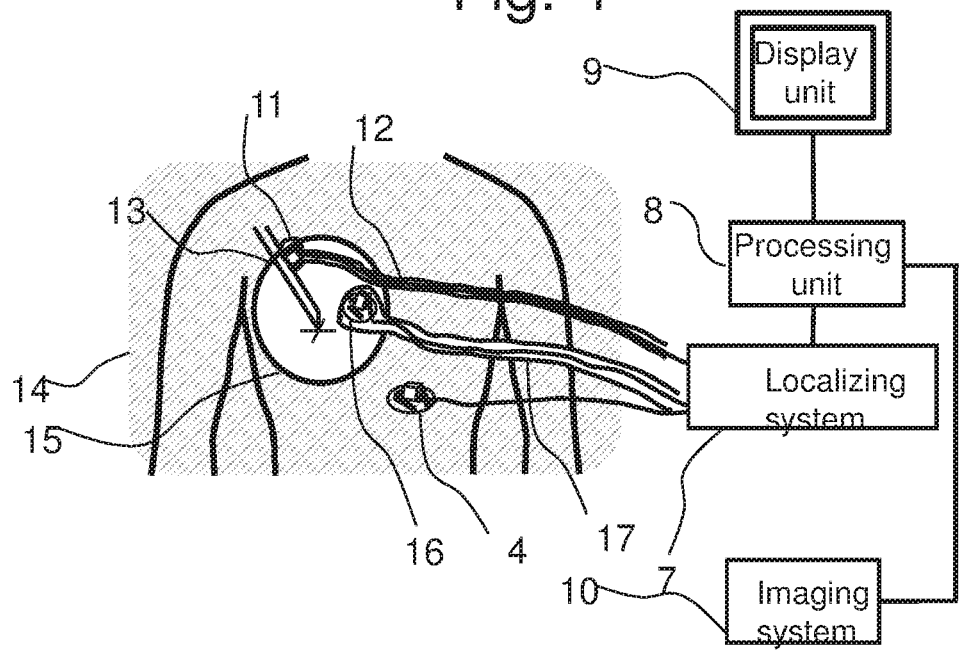

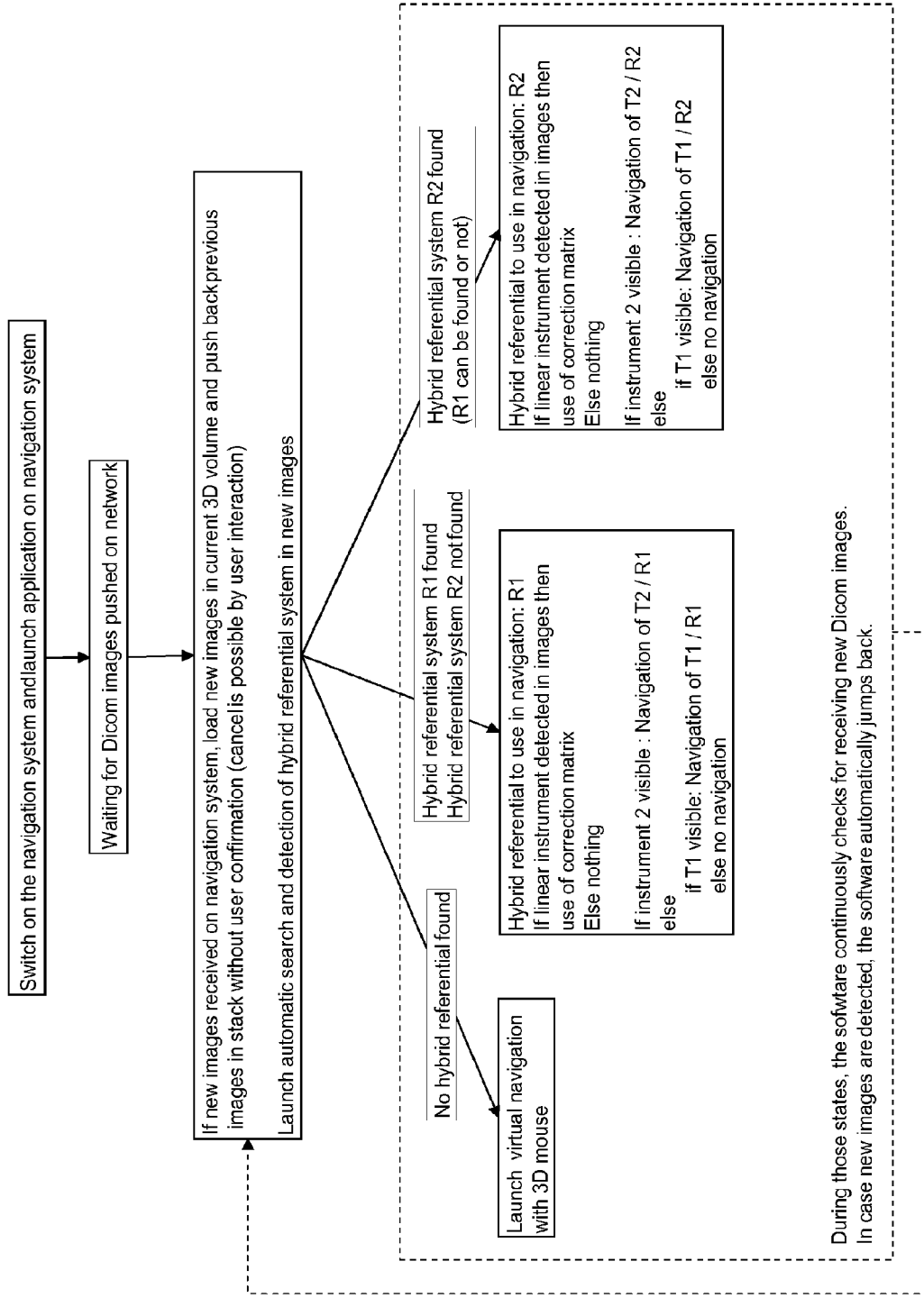

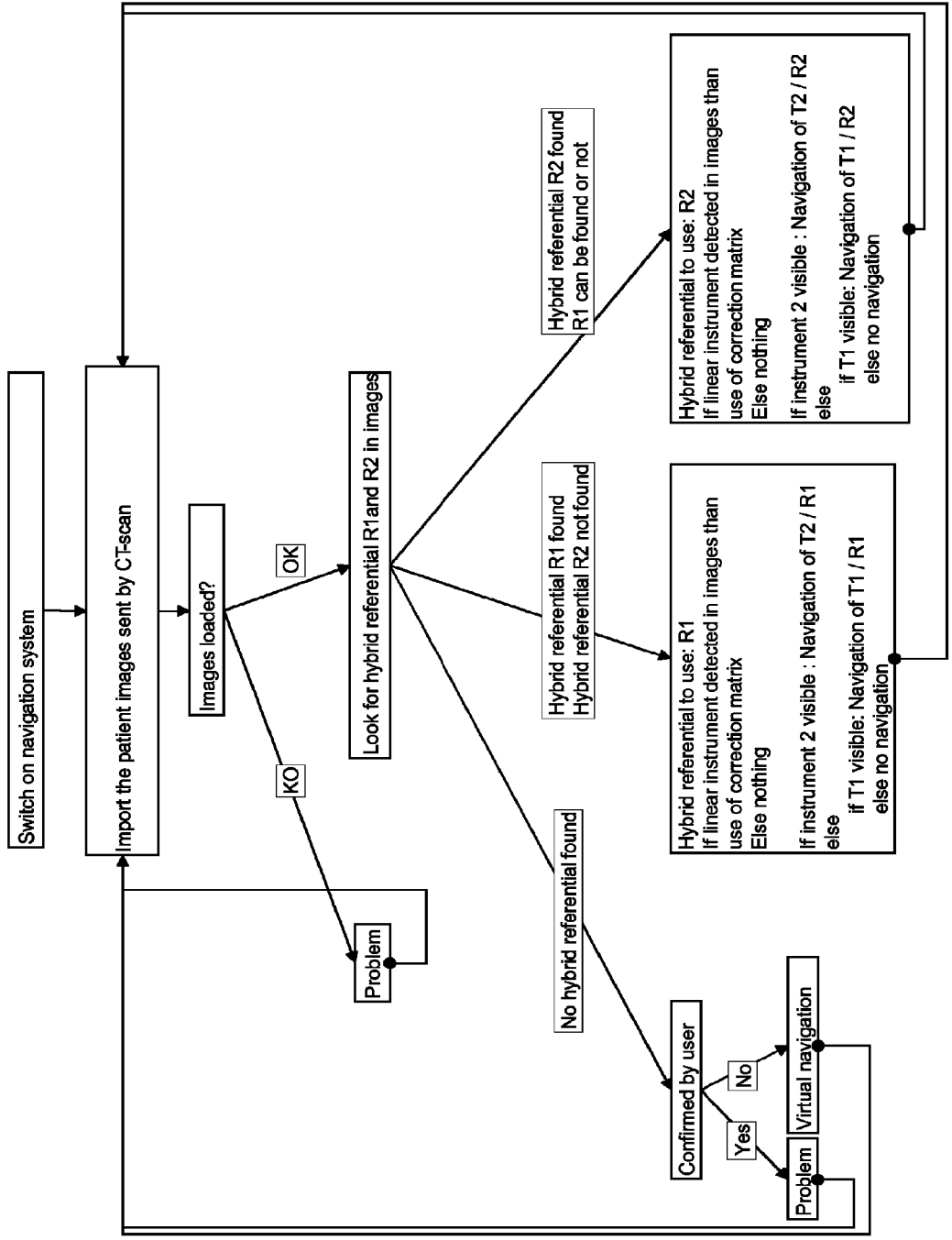

METHOD AND DEVICE FOR NAVIGATION OF A SURGICAL TOOL

CROSS REFERENCE TO RELATED APPLICATIONS

This application is a Continuation of U.S. application Ser. No. 13/146,206, filed Jul. 26, 2011, which is a §371 National Stage Application of PCT/EP2010/050999, filed Jan. 28, 2010, which claims the benefit of U.S. Provisional Application No. 61/148,122, filed Jan. 29, 2009, the content of all of which are incorporated herein by reference in their entireties.

BACKGROUND

Field of the Invention

The invention relates to a method and device for navigation of a tool to be used in a surgical intervention for treating a target region within the body of a patient.

Description of Related Art

Conventional surgical interventions performed in interventional radiology, without any navigation system, consist in introducing a tool, such as a needle or equivalent, in the body of the patient. The interventional radiologist uses an imaging system, most likely a Computed Tomography Scan (CT-Scan) or a Magnetic Resonance Imaging system (MRI), to see the organs of the patient and choose the target for the tip and trajectory of the needle.

In order to help the interventional radiologist to reach the target, a navigation system is necessary. Such systems have been developed for neurosurgical interventions for example. Those systems use a localizing system, also called tracking system, based on optical, electromagnetic, radiofrequency, acoustic (sonar) or mechanical technology. The objective of the localizing system is to give the spatial position and orientation in real time of one or more trackers. The tracker position and orientation is given relatively to the localizing system itself or relatively to another tracker.

An example of such localizing system is based on the electromagnetic technology. More precisely the localizing system comprises an emitter which emits a magnetic field generated by coils, and a tracker operating as a receiver which measures the magnetic field around itself when positioned in the emitted magnetic field. Those measures are sent to a computer system that calculates the position and orientation between the emitter and the trackers (receivers). Those magnetic systems are very ergonomics and easy to use because no direct visualization is required, such that some obstacles may be positioned between the emitter and the tracker (a hand, a surgical drape for example) without any impact on the accuracy of the measurement. One of those magnetic systems is for instance the Aurora device produced by Northern Digital Inc. (Waterloo, Ontario, Canada) or the Patriot device produce by Pohemus Inc. (Colchester, Vermont, USA). However, the measurement precision is better when the distance between magnetic emitter and magnetic tracker is as small as possible.

Some navigation systems using magnetic localizer technology have been developed and used to track the tip of needles in CT images, during an intervention performed inside the CT room directly. One of those systems is for instance the device produced by Traxtall (Ontario, Canada). However, those systems have two major drawbacks. First, they are not always accurate, particularly when the distance between the tip of the needle and the magnetic emitter is not small compared to the distance between the tip of the needle and the metallic table that generates artefacts. Inaccuracy can reach more than 5 millimetres which is not acceptable. Further, the existing systems are complex to use and need user interaction.

The object of the present invention is to provide a method and device for navigating a tool which solve at least one of the drawbacks mentioned above.

In particular, an object of the invention is to provide a method and device for navigating a tool which is very precise, and at the same time enable the practitioner to intervene quickly on the patient.

Another object of the invention is to provide a method and device for navigating a tool which may be fully automatically operated, without requiring any particular action from the practitioner.

SUMMARY

In order to attain the above-mentioned object, the invention proposes a method and a device for navigation of a tool as defined in the claims.

In particular, there is provided a method of navigation of a tool to be used in a surgical intervention for treating a target region within the body of a patient, characterised in that it comprises the following steps for preparing the navigation:

Detecting the image position of a first reference marker disposed on the body of the patient by an image system, and detecting the spatial position of said first reference marker by a localizing system, Calculating a first transform matrix between the image coordinate system of the imaging system and the spatial coordinate system associated with the first reference marker by using detected image and spatial positions of the first reference, in order to register data of the localizing system and imaging system together, Detecting the spatial position of a pointer by the localizing system, Constructing and displaying a navigation image, wherein a representation of the spatial position of the pointer is displayed on image data from the imaging system using the first transform matrix, Detecting the image position and spatial position of a second reference marker disposed under sterile conditions on the body of the patient in the vicinity of an entry point, said entry point being determined by using the representation of the pointer in the navigation image and corresponding to a point through which the tool should be inserted for reaching the target region, Calculating a second transform matrix between the image coordinate system of the imaging system and the spatial coordinate system associated with the second reference marker by using detected image and spatial positions of the second reference, in order to register data of the localizing system and imaging system together.

Alternatively, the method of navigation of a tool to be used in a surgical operation for treating a target region within the body of a patient is characterised in that it comprises the following steps for preparing the navigation:

Disposing a first reference marker on the body of the patient,

Detecting the image position of said first reference marker by an image system, and detecting the spatial position of said first reference marker by a localizing system, Calculating a first transform matrix between the image coordinate system of the imaging system and the spatial coordinate system associated with the first reference marker by using detected image and spatial positions of the first reference, in order to register data of the localizing and imaging systems together, Detecting the spatial position of a pointer by the localizing system, Constructing and displaying a navigation image, wherein a representation of the spatial position of the pointer is displayed on image data from the imaging system using the first transform matrix, Determining an entry point through which the tool should be inserted for reaching the target region by using the representation of the pointer in the navigation image, Disposing a second reference marker under sterile conditions on the body of the patient in the vicinity of the entry point, Detecting the image position and spatial position of said second reference marker, Calculating a second transform matrix between the image coordinate system of the imaging system and the spatial coordinate system associated with the second reference marker by using detected image and spatial positions of the second reference, in order to register data of the localizing and imaging systems together.

This navigation method is therefore very advantageous as it enables performing navigation of a tool by using a second reference marker which is positioned very near from the entry point through which the tool (e.g. needle) is to be inserted for reaching the target region. Therefore this enables minimizing the distance between a magnetic emitter, preferably placed in the second reference marker, and the magnetic tracker placed in the tool, and thus enhances the measurement precision, in particular because it reduces the effect of the artefacts generated by metallic elements in the room, such as the metallic table.

Such method further enables disposing the second marker under sterile conditions, and at the same time very near from the entry point.

Preferred but not limiting aspects of these navigation methods are the following:

The method further comprises the step of imaging a zone of the body of the patient with the imaging system to get image data of the zone, said zone including the entry point.

The method further comprises the step of searching for the presence of the first and second reference markers on the image data of the imaged zone, and
  in case the second reference marker is present on the image data of the imaged zone, then constructing a navigation image wherein registration of the data of the localizing systems together with image data of the imaged zone is performed by using the second transform matrix,
  in case the first reference marker is present on the image data of the imaged zone whereas the second reference marker is not present, then constructing a navigation image wherein registration of the data of the localizing systems together with image data of the imaged zone is performed by using the first transform matrix.

The method further comprises the steps of searching for the presence of the tool with the localizing system, and
  in case the tool is present,
    determining the spatial position of the tool, and
    constructing and displaying a navigation image, wherein a representation of the spatial position of the tool is displayed on the image data from the imaged zone.

In case the tool is present, it further comprises the step of searching for the presence of the pointer with the localizing system, and in case the pointer is present, determining the spatial position of the pointer, and constructing and displaying a navigation image, wherein a representation of the spatial position of the tool is displayed on the image data from the imaged zone.

The method comprises correcting the navigation data, said correction comprising the steps of:
  searching for the presence of linear shapes on the image data of the imaged zone,
  selecting the linear shape having the nearest position from the position of the tool on the navigation image,
  compute a correction matrix to make the position of the tool on the navigation image correspond to the position of the selected linear shape, and
  apply said correction matrix to the construction of further navigation images.

The step of imaging a zone of the body of the patient is regularly and automatically performed, and wherein the subsequent steps are performed using the last image data of the imaged zone.

The localizing system is based on magnetic detection, and the imaging system is based on X-ray detection.

According to another aspect of the invention, here is provided a navigation device for performing the above method of navigation characterised in that it comprises:
  an imaging system for providing image data relative to the patient,
  a localizing system for providing spatial data,
  a computer system for processing the image data and spatial data from the imaging system and localizing system respectively,
  at least a first reference marker and a second reference marker adapted to be detected by both the imaging and localizing systems, wherein the second reference marker is sterile.

Preferred but not limiting aspects of this navigation device are the following:

The localizing system is a magnetic tracking system.

Each of the reference markers comprises:
  a magnetic element having at least two coils arranged in a manner to define at least two vectors in the coordinate system of the magnetic tracking system;
  a geometric element comprising components visible on image data of the imaging system and having a unique geometry detectable by the imaging system.

The reference markers comprise magnetic elements having coils arranged in a different manner, and geometric elements having components of different shapes and/or arranged in a different manner.

The magnetic tracking system comprises at least an emitter for emitting an electromagnetic field.

The emitter is the magnetic element of the first reference marker and/or the magnetic element of the second reference marker.

The device further comprises tracking elements adapted to be arranged on the pointer and/or on the tool to be used in the surgical operation for treating the target region within the body of a patient, such tracking elements being adapted to be detected by the tracking system.

The tracking elements are connected to the pointer and/or the tool with a connecting device, said connecting device comprising means for fixing pointers and/or tools of different diameters always along the same axis.

The tracking elements are connected to the pointer and/or the tool with a connecting device, said connecting device comprising clamping means for fixing the pointer and/or the tool on said connecting device, said clamping means being adapted for allowing the pointer and/or the tool to slide relative to the connecting device on application of a pressure on said clamping means. The imaging system is a Computed Tomography (CT) imaging system.

BRIEF DESCRIPTION OF THE DRAWINGS

Other characteristics and advantages of the invention will become clear from the following description which is only given for illustrative purposes and is in no way limitative and should be read with reference to the attached drawings on which:

FIG. 1 is a representation of a marker usable with the navigation method and device of the invention;

FIG. 2 is a representation of a step of preparation in the navigation method of the invention;

FIG. 3 is a representation of a further step of preparation in the navigation method of the invention;

FIG. 4 is a representation of a step of navigation of the tool in the navigation method of the invention;

FIG. 5 is a diagram representation of the operation of the navigation method according to a first embodiment;

FIG. 6 is a diagram representation of the operation of the navigation method according to a second embodiment.

DETAILED DESCRIPTION OF A PREFERRED EMBODIMENT

Figure 7:
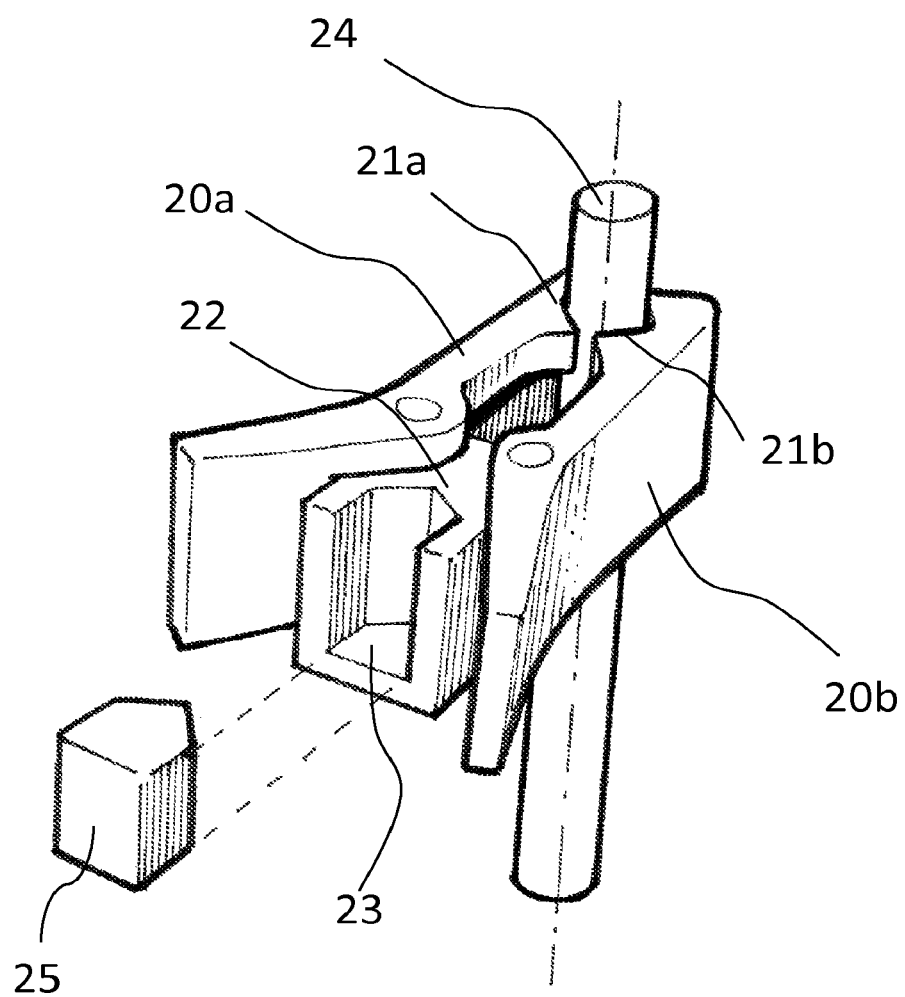
FIG. 7 is a representation of a connecting device for fixing a tracker on a surgical instrument.

The navigation method and device of the invention are described hereafter with reference to a Computer Tomography (CT) imaging system based on X-rays, and a magnetic localizing system. The principle of the invention may however be used in any systems, such as imaging systems based on X-ray, magnetic resonance imaging or ultrasound imaging.

Navigation systems based on magnetic technology generally comprise a magnetic emitter box which is positioned close to the patient. A reference marker operating as a tracker or receiver is fixed to the skin of the patient. This reference tracker is made of one or several coils to be detected by the magnetic localizing system, and further comprises a geometric element easily visible on images from the imaging system. To be easily visible on the images of the imaging system, such geometric elements are usually made of specific materials and the geometry can be, for example, small spheres, metallic thread, solid or open cylinders, or asymmetrical curvilinear shapes.

The geometric elements are thus detected in images from the imaging system and used to register the surgical world with images of the patient. Consequently, the reference marker enables defining a common referential system in being detected by both the imaging and localizing systems, so that data of the localizing and imaging systems may be registered together.

Then, a magnetic tracker may be fixed on the tool to navigate, such that the magnetic localizing system computes the position of the tool, on which a magnetic tracker is fixed, relatively to the reference tracker on the skin of the patient, and then the registration correlates the reference tracker on the skin of the patient with images from the imaging system.

As a result, the position of the surgical tool can be correlated to the images of the patient, allowing the system to virtually display the surgical instrument in the images of the patient. Indeed, the registration enables constructing and displaying a navigation image, wherein a representation of the spatial position of the tool is displayed on image data from the imaging system using the referential system defined by the reference marker.

As already mentioned, minimising the distance between magnetic emitter and magnetic tracker is an important issue for accuracy of the spatial position data from the localizing system. The problem is that, in case the reference tracker has been fixed on the skin of the patient far from the instrument position, that is far from the entry point through which the instrument is to be inserted, then it is necessary to change the position of the reference tracker fixed on the skin of the patient and restart the imaging process if the practitioner does not want to navigate the tool with a navigation device based on potential inaccurate measurements. Further, positioning or repositioning of the reference marker near the entry point is not always easy as it should be made under sterile conditions, which is usually not the case before imaging the patient.

The challenge is thus to use a navigation system based on magnetic technology while keeping a maximum of precision and respecting the usual sterilization process.

The complete navigation procedure should also be faster than conventional navigation methods, so the system is very simple to use.

Preferably, the reference marker is used for providing a hybrid referential system in the surgical world. It should be noted that the terms "reference marker" or "hybrid referential system" may be used indifferently in the rest of the description. The reference marker is used for calculating a registration transform matrix between spatial data of the localization system and image data of the imaging system.

The reference marker is preferably a device having a fixed and known geometry known by calibration that includes two components: first, a magnetic tracker that is identified in a unique manner by the localization system and second, a geometric tracker visible on CT images and having a unique geometry.

FIG. 1 illustrates an embodiment of such a reference marker 4 comprising a magnetic tracker 3, a geometric tracker 2, and an element 1 for fixing the reference marker on the skin of the patient.

The magnetic tracker can be an emitter with at least two coils or a receiver with at least two coils in order to define at least two vectors which define a coordinate system in three dimensions.

The geometric tracker is for example made of two or three hollow aluminium tubes with inner diameter of 1 mm and outer diameter of 2.5 mm, with those tubes being arranged such that they make specific and unique known angles between them. Those angles will be three or more specific values for a first hybrid referential system R1, and three or more different values for a second hybrid referential system R2 as will be explained after.

In this case, the computer system may comprise a software programmed for searching for linear tubes in a volume of CT images. Usually, each voxel of the volume is compared to a threshold value in Hounsfield units that corresponds to the value of density expected for tubes. Voxels having the desired value of the tube material plus or minus a predefined noise range are stacked. Then, a variety of image processing algorithms can be used to detect a linear tube in the stack of voxels. Linear tubes having too small or too long length are discarded. Linear tubes having too small or too large diameters are discarded. Then tubes are compared by pairs and the ones having an angle in the list of searched values are stored. If three tubes have three pairs of angles corresponding to one of the searched reference marker hybrid referential system, the corresponding reference marker is assumed to be detected. From this detection, it is then possible to use a standard least squares algorithm in order to compute the transform matrix between the CT image coordinate system and the hybrid referential coordinate system, that is the coordinate system associated to the reference marker, so that the coordinates of the tubes in the hybrid referential system transformed by this matrix match with the coordinate of the tubes detected in the CT image coordinate system. The same principle can be applied if the three or more tubes are replaced by three or preferably four spheres made of metallic balls with diameter ranging from 1 to 5 mm, or by one distorted ellipse made of a metallic thin wire inserted into a plastic housing having a distorted elliptic shape acting as a cast. Many other shapes and material can be used to create a geometric tracker.

In general, reference tubes are made of high density materials such as aluminium for example and a simple thresholding operation on CT images makes the tube detection very easy. All pixels or voxels of images having values superior to the threshold are candidate to be a tube and those candidates are aggregated and the shapes of aggregated voxels or pixels is compared to predefined shape factors such as size, length etc. However, in radiology and computer tomography in particular, it is preferable to avoid introducing high density objects since they may corrupt the quality of the reconstructed images. In particular, the quality of the images can be affected simply by the presence of high density objects that capture the attention of the radiologist since they generate bright spots on the images. Usually this is neglected but there is no proof that this cannot affect the decisions taken from images and therefore a potential risk is introduced.

In order to avoid the presence of high density materials to constitute the tubes, the tubes may be simply made of materials having a specific density N1 for the inner part of the tube and a specific density N2 for the tube material itself. N1 and N2 correspond to known Hounsfield values in the CT images that are low enough to reduce the risk of artefacts and with enough difference between them to make them distinguishable in the presence of noise. Those values can be easily calibrated for any material by performing a test CT and simply noting the Hounsfield values for the corresponding pixels on the images of the materials. In theory, one could use only one density value N1 of a tube, but by searching for two values N1 and N2 in grey level images, the occurrence of false positive detection (shapes having a density value and form factors values equal to searched values) is reduced and reliability of the algorithm is reinforced. In a particular embodiment, the value N1 corresponds to high density plastic and the inner part N2 is simply made of air. The software searches for tubes with an external part having a density in Hounsfield values equal to the plastic material value and an internal part with a null density (density of air in Hounsfield values). Such geometric tracker with hollow tubes or twofold-densities N1-N2 can be used for patient registration in interventional radiology when only one reference marker is used. This occurs when good a priori information is known about the entry point of the needle such that the reference marker can be placed in its vicinity at the beginning of the intervention. It offers the advantage of a robust and automated detection without affecting image quality.

Figure 11:
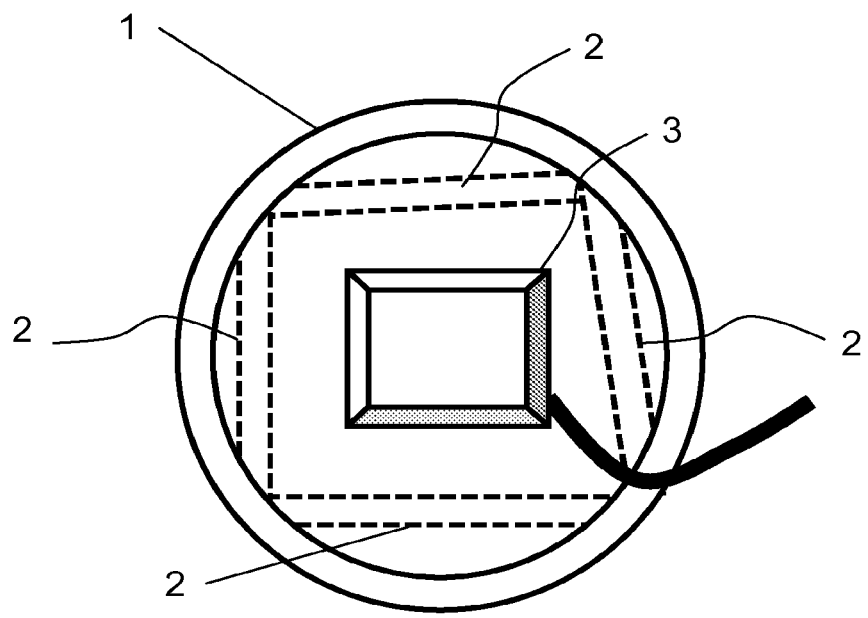
FIG. 11 is a representation of another embodiment of a marker.
Figure 12:
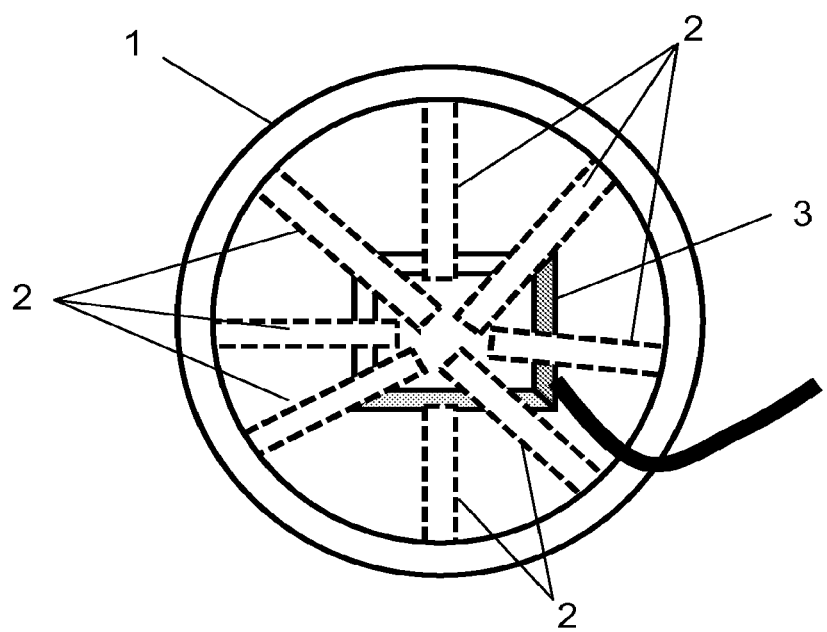
FIG. 12 is a representation of still another embodiment of a marker.

For all of these configurations of the geometric tracker, with solid tubes, hollow tubes, or even twofold-densities tubes, the number of tubes that constitute the geometric tracker is not limited. Thus, a well known N-shape arrangement of three tubes can be used. Alternatively, as illustrated in FIG. 11 (the same sign references are used in this figure to designate the same elements as those of FIG. 1), four tubes can be arranged (for instance hollow tubes in a plastic circular solid shape) to constitute four line segments that are never parallel and such that at least three of them have at least 30° of angle with respect to the longitudinal axis of the CT images, which is usually important since the resolution is often lower along that direction than inside the image plane. On each bidimensional CT image, at least three tubes will therefore generate an intersection with the image plane that is easily and accurately detected. In another preferred embodiment represented in FIG. 12 (the same sign references are used in this figure to designate the same elements as those of FIG. 1), which presents the advantage of being easy to machine, eight tubes (for instance hollow tubes in a plastic circular solid shape) are arranged spatially to constitute a star, all tubes intersecting roughly in the centre of the star. Having several line segments reinforces the accuracy of the registration technique by using well known least-squares methods for registration between lines.

As illustrated in FIGS. 2 to 4, the navigation device comprises a computer system comprising a processing unit 8 and a display unit 9. The navigation device further comprises an imaging system 10, such as a CT-scan, and a localizing system that includes a localizer control unit for emission and detection of magnetic field. The computer system is preferably connected to the network in order to be able to receive DICOM images from the CT workstation.

The overall operation of the navigation device is the following.

When a new session is launched, the computer system has a void stack of images. When the radiologist pushes CT images from the CT workstation, the software automatically detects those images using a well known DICOM communication protocol. The new images are read and put in the current stack immediately without user interaction. A volume is automatically reconstructed from the list of 2D images in order to build a volume of homogeneous voxels, so called 3D image, using standard methods.

Then, without any user interaction, the software searches for a hybrid referential system in the current 3D image that is a reference marker is searched.

Then navigation is enabled by using one of the detected reference markers disposed on the body of the patient.

Detection of the best candidate as an hybrid referential system is made automatically by the computer system such that the navigation method and device may be operated fully automatically which is a great advantage as the practitioner does not have to worry about anything but to correctly insert the surgical instrument within the body of the patient.

The first step of the navigation method of the invention is illustrated in FIG. 2.

A first hybrid referential (R1) is fixed on the skin of the patient. This is reference marker 4 as illustrated on FIG. 2.

The hybrid referential system is positioned anywhere on the body of the patient, provided it is located within the field of the imaging system. As such first reference marker is disposed under non-sterile conditions, it is preferable not to place it in a zone of the skin of the patient where it is probable to have the entry point (which should be under sterile conditions during the surgical operation).

Two cases exist with regard to the first reference marker. Indeed, reference marker R1 may be a small magnetic emitter, such that any tracker (receiver) may be localized with this emitter. In another case, reference marker R1 may be a magnetic tracker, receiver (sensor). In this latter case, the emitter is in a box fixed to an articulated arm or it is fixed also on the skin of the patient, such box being manipulated by the radiologist to correctly position the emitter in a relative position not far from the tracker. In both cases, the navigation method will be exactly the same.

A first 3D image of the patient is acquired with a large field of view. The images are transferred to the computer system of the navigation station. The software fully automatically searches for the geometry of reference marker R1 in the images.

In case reference marker R1 is not detected in the images, it means that the images have been done without any hybrid referential system i.e. it suggests that there is no new patient in the CT scan gantry. This is possible in case the radiologist has loaded diagnostic images of the patient. In this case, the navigation process will be done in an arbitrary referential. This process allows a fast and accurate examination of the patient's anatomy with an instrument like a 3D mouse or directly a phantom of the instrument, like a pen, equipped with a tracker. It also allows anticipating the fact that a target is reachable or not. Up to date, to check if a target region to be treated can be reached, the radiologist works in 2D on axial images of the patient. While comparing the current standard process for patient's anatomy examination and the process our innovation provides, the advantage is quickly seen. In this case, one refers to virtual navigation.

In case reference marker R1 is detected in the images, then all dimensions and geometry are checked to ensure that it is really reference marker R1. Reference marker R1 being detected, the registration process may be performed: the transform matrix between R1 coordinate system and the CT images coordinate system is determined by using standard registration methods between geometric features.

A magnetic tracker 6 is then fixed on an instrument 5 that allows drawing of an entry point on the patient skin, such instrument being also called a pointer. The pointer is navigated with regards to R1 using the magnetic trackers. Combining magnetic localisation and registration process, the pointer can be displayed in the images of the patient, on a so called navigation image which is displayed by the display unit 9.

The pointer 5 is a kind of navigated pen or template that allows the radiologist to find the best trajectory in order to reach the anatomical target region and the entry point on the skin of the patient. When the entry point is determined, then the radiologist can draw a sign on the skin of the patient to mark the entry point such as a dot point, a cross hair or a circle. During this step, the software computes and displays, for example, two slides passing through the instrument axis in real-time or a 3D view of the patient anatomy with a projection of the instrument, like in any surgical navigation system.

At the end of this first step, the radiologist has found and saved in the computer the best trajectory to reach the anatomical target. To save the trajectory in the computer can be done with a touch screen, or a footswitch or a manual control. During all the further steps it will be possible to save another trajectory. The last saved trajectory will always be displayed, so that the radiologist can always remember the last trajectory that has been saved and can use it as a reference.

Further, the radiologist has made a mark on the skin of the patient to know and remember the entry point. In case the patient is not correctly positioned on the imaging system table, the radiologist can then change the patient position so that the trajectory becomes more accessible and the surgical gesture becomes more comfortable.

The subsequent step consists in providing a second reference marker in the vicinity of the entry point which has been determined through the navigation of the pointer in first hybrid referential system R1 (see FIG. 3). Such second reference marker 16 will be preferably used for navigating the surgical tool as is explained after.

In this step, the radiologist prepares the sterilization. It is done by spreading the skin of the patient with sterile liquid around the entry point and using a sterile drape with an open space. The first hybrid referential system R1 will be under the sterile drape as it has not been disposed in a zone around the alleged entry point. The radiologist also becomes sterile by changing his clothes, washing his hand and using gloves.

Then, the radiologist fixes on the skin of the patient a new hybrid referential system R2 (second reference marker 16) close to the entry point of the instrument before any control imaging process. Contrary to first reference marker R1 that was non sterile, second reference marker R2 has to be sterile since it will be fixed in the sterile field. The hybrid reference marker can be made sterile by simply inserting it within a sterile cover, or by sterilizing said reference marker with standard techniques of sterilization.

Second reference marker R2 may have the same structure of first reference marker R1 with slightly modified distances. It can namely be used as an emitter or a receiver. It can contain hollow tubes or tubes with twofold density materials.

Similarly to the first reference marker R1, when second reference marker R2 is detected in the images, then the registration process may be performed: the transform matrix between R2 coordinate system and the CT images coordinate system being determined, in order to map data from the localizing and the imaging systems together, and eventually construct a navigation image.

As the second reference marker R2 is disposed closer to the entry point, it will be located closer to the navigated instrument that is provided with a magnetic marker, which enables a more accurate navigation. Indeed, the magnetic localization is more precise since the second hybrid referential R2 and the surgical tool are close to each other, and the distance between them is smaller compared to the distance between the operating table and any of both magnetic trackers, which reduces possible artefacts. Indeed, the recommendation from several magnetic localizing systems manufacturers is to have a distance between the emitter and receiver five times less than the distance between emitter/receiver and metallic objects that generate artefacts. Further, the second patient referential R2 follows more precisely the motion of organs that can be due to breathing for example since it is likely to be the closest to the organs that are targeted.

The navigation process has now been fully prepared, and the practitioner can begin the intervention with the necessary surgical instrument, said instrument being navigated with the improved navigation device of the invention as illustrated in FIG. 4.

A magnetic tracker 11 is fixed on the surgical instrument 13 so that the surgical instrument may be detected by the localizing system. As the intervention is made under sterile conditions, the magnetic tracker 11 is sterilized, or inserted within a sterile cover 12, and fixed with a sterile connection to the sterile instrument 13.

The surgical instrument can be different depending on the medical indication and the intervention to perform. It can be a needle, a needle guide, a troccard or any other linear instrument. In any case, the instrument diameters can be different and usually range from 1 mm to 6 mm.

In case the instrument is a guide, only the axis of the needle introduced in the guide will be navigated. The depth penetration of the needle is monitored using the marks drawn on the needle (a scale is usually written on standard instrument to measure the depth penetration) and the images displayed by the navigation system are used to measure the planned distance between the skin and the target. Measuring the position of a guide has the advantage that the magnetic emitters and receivers remain close to each other which is not the case if a miniature sensor is fixed to the needle tip since the latter will be closer and closer from the table during a deep insertion.

By using the navigation device described, the radiologist can monitor the position and orientation of the instrument using the navigation images displayed on the screen, and he can thus start to introduce the instrument.

As the second reference marker R2 is fixed on the skin of the patient in the vicinity of the entry point, the imaging process can be performed on a smaller volume than during diagnostic imaging process as the region of interest is known and the radiologist has only to focus on the surgical instrument and the target. This allows decreasing patient exposure to X-rays.

Once the navigation system receives new images of the patient, they are loaded and the system searches if the first reference marker R1 and/or the second reference marker R2 are visible in the images.

To distinguish the first reference marker R1 from the second reference marker R2, the geometric markers are different in the first reference marker R1 and in the second reference marker R2 (difference can be done by number of visible components, angles between tubes, geometry, diameter of tubes, spheres or cylinders . . . ).

In case the second reference marker R2 is visible in the images, whatever if the first reference marker R1 is visible or not, then the surgical tool is navigated with respect to the second hybrid referential systems R2. The spatial data being more accurate when using the second reference marker R2, then the navigation method has an increased precision. The radiologist now benefits from the most accurate information given by the navigation system.

In case only the first reference marker R1 is visible in images, as may for example be the case if there is a failure in the operation of the second reference marker R2, or if the user has decided that the accuracy would be sufficient with the use of only R1, then the surgical tool is navigated with respect to the first hybrid referential system R1. Consequently, the surgical tool may still be navigated, even if the navigation is not as precise as with respect to the second reference marker R2.

Figure 13:
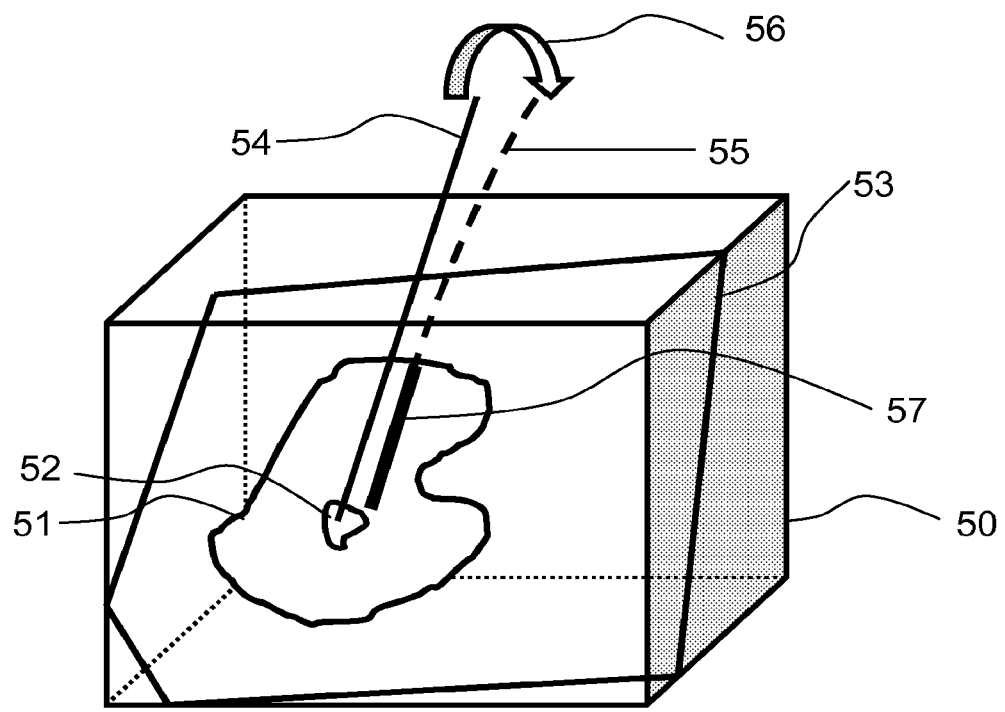
FIG. 13 is a representation of a method of correction of the navigation method according to an embodiment of the invention.

As illustrated in FIG. 13, in case the anatomical organs 51 are mobile under the influence of the patient's breathing or if the target 52 is small or difficult to reach, the radiologist can freely iterates between instrument introduction and control imaging process. As a result, the practitioner will be able to accurately check the position of the instrument during its progression since the instrument is visible as a trace 55 in the volume of images 50, which is a 3D curve in theory but mostly contained in an image plane 53. During the navigation with the navigation device, the real instrument trajectory 55 (visible in images) should perfectly fit with the virtual position 54 of the instrument displayed by the navigation system.

If a small offset exists, for any kind of reasons (for example, patient breathing or system inaccuracy), the navigation system software will compute this offset thanks to an image processing technique. For example, the software can search for and detect a linear or curvilinear tool 55 in images close to the last navigated position of the instrument. Since needles are usually made of metals, this operation can be performed by applying a threshold on the images and searching for long and thin aggregations of voxels. Standard mathematical morphology tools well know in image processing can be used. The software will then automatically compute a correction matrix 56 to register the virtual position of the instrument 54 to its real position 55 detected on the images. A correction matrix that is a transform matrix made of 3 rotations and 3 translations is computed that creates a best-fit coincidence between the theoretical position of the needle and the real needle approximated by a line segment 57 in its terminal part which is detected in CT images. All the degrees of freedom of this matrix are not perfectly fixed, since the registration of a line to a line solves only 4 degrees among the 6 degrees of a transform matrix.

The computer may then arbitrary set the last two free degrees of freedom to zero; knowing this will have no impact on the accuracy as the first degree is around the axis of the instrument and that the second is the translation along the axis of the instrument. The correction matrix is then applied during all the next steps of navigation until new patient images processing is done. This correction process can be used for patient registration in interventional radiology when only one reference marker is used. This occurs when good a priori information is known about the entry point of the needle such that the reference marker can be placed in its vicinity at the beginning of the intervention. It offers the advantage of an accurate detection and registration after the CT control images have been acquired. It makes full use of the most updated images that are usually acquired for control and check, and it takes into account all parameters of deformation that cannot be known by simple rigid models of the transform between the reference marker and the patient images.

As seen above, the navigation method of the invention includes different steps. FIGS. 5 and 6 are diagrams illustrating those different steps of the navigation method.

It is important to note that the choice between the different steps is done automatically depending on the result of the automatic detection of the hybrid referential system.

Thanks to this automatic detection of hybrid referential system, there is no need for human interaction to select what has to be done by the navigation system. It means that the navigation system is automatically adapted to what the user wants to do. The full process can thus be performed with zero interaction between the user and the user interface of the system.

The ability to have a full automatic navigation method is very important and leads to several advantages:
- Reduction of the human-machine interaction;
- Facilitation of the use of navigation;
- Reduction of the learning curve;
- Opening interventional treatments to non-experimented users;
- Elimination of the user's error;
- No constraint for the user of the way to use the navigation device;
- Navigation becomes an intelligent and adapted assistant tool in order to reach the optimal accuracy.

More generally, one important particularity of our invention is that our method does not need the user input in any step of the protocol, and this not only in the selection of the best hybrid referential system to use.

The idea is that our algorithm selects default choices in the computer memory and applies those choices, instead of having the user to interact with the system to answer questions like YES or NO, or select an image in a list for instance, or also select the next step in a list of possibilities.

At the very first step of our system, once the system has been switched on and a connexion has been set up with the CT imaging device through a standard Ethernet port for instance, the software is automatically launched. If several software applications run on the system, this is accomplished by providing an electronic key, such as a Smart Card or a USB key that launches the desired application. Then the software starts waiting for DICOM images to arrive on the system. Once images are detected, the system optionally checks that they come from the CT imaging device that is referenced, and those new images are immediately loaded in the memory of the computer, erasing previous images without asking to the user if those images are the one he/she wants.

The automatic protocol is the default mode but the user can still have the possibility to take the control back. For instance, if the new images are not correct, then the user can touch a button on the screen of the system and retrieve the old images using a variety of menus.

As already detailed, once the images are loaded in the memory of the computer, the software launches automatically a process to search for hybrid referential systems R1 and R2. Based on the results of the search, the software selects the next step automatically using the algorithm detailed above.

In addition, preselected options of the user can be stored in the computer memory or in the electronic card that launches the application so that they are applied automatically without selecting them again. Those options are for instance the type of visualization mode preferred by the user during navigation. It can be one window image only, two windows, or a three-dimensional view, or two planar images displayed in a 3D scene with a perspective mode, and a variety of other modes, or any combination.

Once the protocol has been completed, that is after the end of the procedure, the user interacts with the system to press the exit button in order to switch off the system properly.

Note that this fully automated algorithm works also if there is only one hybrid referential system used.

As mentioned above, the surgical instrument to navigate is attached to a tracker to be detected by the localizing system.

The instrument would be preferably implemented by using a connecting device as shown in FIG. 7, such connecting device enabling a secured fixation of the tracker on the surgical instrument.

This connecting device is advantageous as it is in particular adaptable to all instruments with a diameter ranging from 1 to 6 mm and has an axis position which is identical with an error which is less than 1 mm.

The connecting device is composed of two articulated arms (20a and 20b) connected by a base (22) which supports the tracker connection interface (23) with which the tracker (25) can be connected. This interface will be further referred to as tracker slot. Note that the articulation between the arms and the base can either be achieved by means of an axis or with a flexible area (ails parts being a single one in this embodiment).

The connecting device is maintained in position on the instrument (24) by mean of a clamping mechanism composed of two grooves facing each other (21a and 21b). The device incorporates a spring that applies a force to the instrument so that there is no play left when the clamp is released by the user.

The device is designed so that the two articulated arms move in a symmetrical manner relatively to the base. This can be achieved either with gears on each arms engaging each other or simply by having two identical loaded springs on each arm. These identical springs will make sure that when the device is clamped its balance position will be symmetrical.

This symmetrical movement disposition makes sure that the instrument axis (24) position does not change relatively to the tracker slot when the instrument diameter changes.

Figure 8:
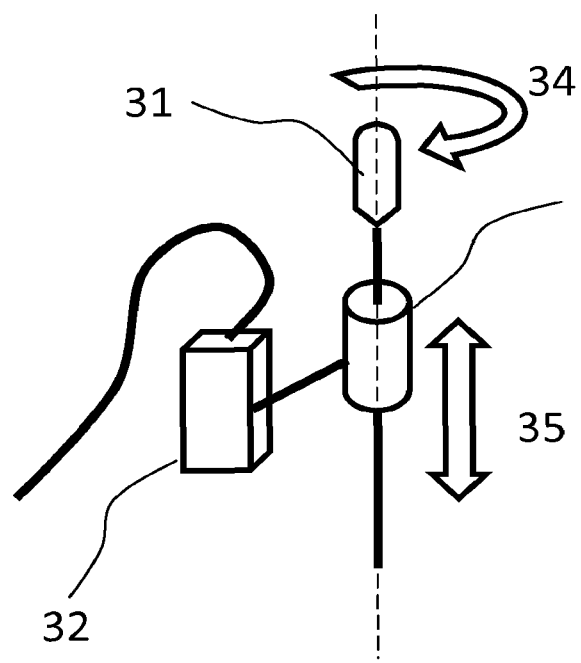
FIG. 8 is an illustration of the operation of the surgical instrument with a tracker fixed with the connecting device of FIG. 7.

As illustrated on FIG. 8, the connecting device creates a sliding pivot link between a tracker (32) and a navigated instrument (31). While the device is mounted, the instrument is still able to slide (35) and rotate (34) along its main axis relatively to the connecting device if a slight pressure is applied by the user. This link can be destroyed at anytime by simply removing the connecting device from the navigated instrument. If no pressure is applied, the navigated instrument remains fixed to the connecting device.

Figure 9:
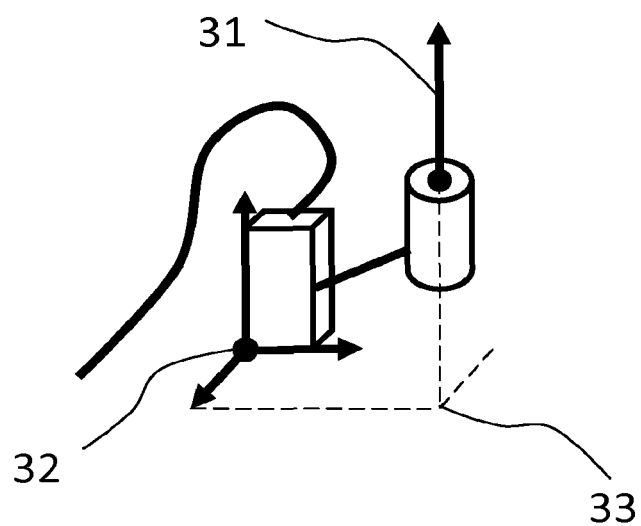
FIG. 9 is a further illustration of the operation of the surgical instrument with a tracker fixed with the connecting device of FIG. 7.

As illustrated on FIG. 9, the connecting device is designed and built in so that the relation between the tracker (32) and the axis position and orientation of the instrument (31) is perfectly known within the tracker reference (33). More importantly, the clamping mechanism ensures that the same position is obtained each time the instrument is removed and replaced into the device.

Figure 10:
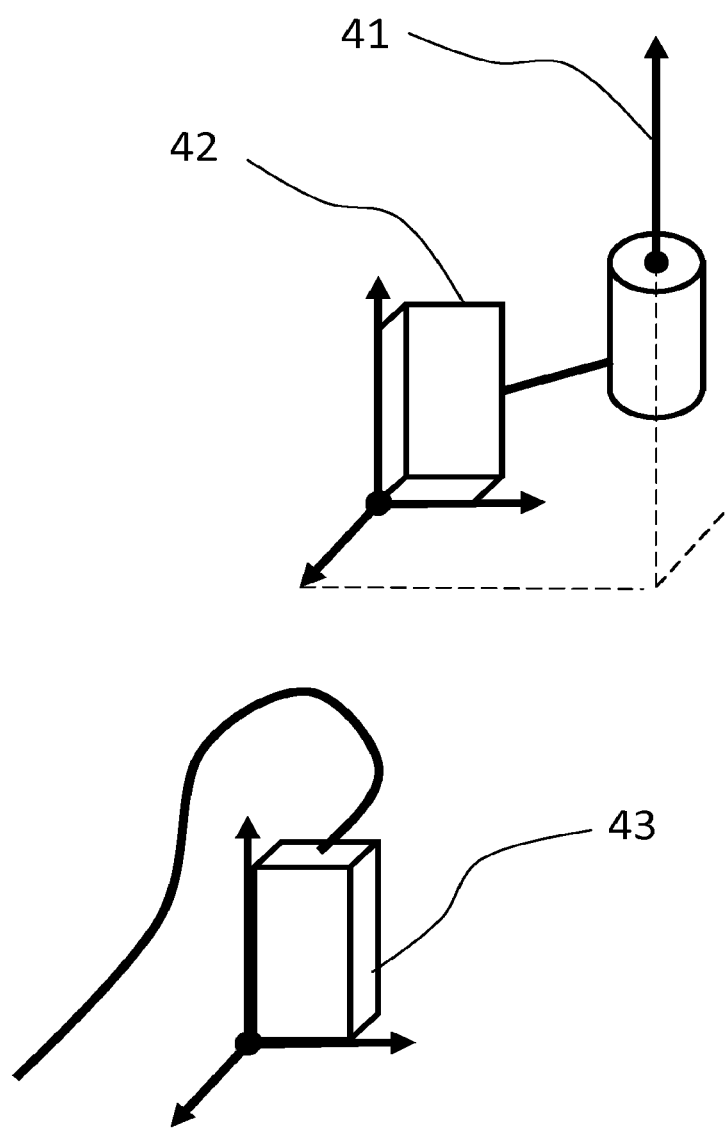
FIG. 10 is an illustration of the operation of the surgical instrument with a tracker fixed with another embodiment of the connecting device.

As illustrated in FIG. 10, the tracker (42) can, in another embodiment, be provided as a separate element from the connecting device. The connecting device then incorporates two reproducible clamping fixations: one for the tracker and one for the navigated instrument. The clamping mechanism for the tracker creates a full link, without any degree of freedom left. The device is then built in such a way that the instrument axis position and orientation (41) is precisely known relatively to the tracker connection interface (42).

The connecting device can be used for tracking a needle in interventional radiology when only one reference marker is used. This occurs when good a priori information is known about the entry point of the needle such that the reference marker can be placed in its vicinity at the beginning of the intervention.

The reader will have understood that many modifications may be made without going beyond the new information and the advantages described herein. Consequently, all modifications of this type shall be within the scope of the navigation method ad device described here.

The invention claimed is:

1. A method of navigation of a linear instrument to be used in a surgical intervention for treating a target region within the body of a patient, comprising detecting by an imaging system an image position of a reference marker disposed on the body of the patient in a vicinity of an entry point corresponding to a point through which the linear instrument should be inserted for reaching the target region, and detecting a spatial position of said reference marker by a localizing system, calculating a transform matrix between an image coordinate system of the imaging system and a spatial coordinate system associated with the reference marker by using detected image and spatial positions of the reference marker, in order to register data of the localizing system and imaging system together, applying a correction matrix to said transform matrix so as to determine a corrected transform matrix, wherein said correction matrix is computed by the following steps:

obtaining image data of a zone of the body of the patient with the imaging system, said zone including the target region to be treated and at least a part of the linear instrument;

displaying a real position of said part of the linear instrument as a linear trace visible on the image data;

determining a virtual position of the linear instrument with the localizing system using a magnetic tracker attached to the linear instrument or to a guide of the linear instrument; and computing the correction matrix so as to make a position of the linear instrument on a navigation image correspond to a position of a selected linear shape using said linear trace and said virtual position;

detecting a spatial position of the linear instrument determined by the localizing system; and constructing and displaying the navigation image, wherein a representation of the spatial position of the linear instrument is displayed on said image data from the imaging system using the corrected transform matrix.

2. The method of claim 1, wherein the step of obtaining image data of the zone of the body of the patient is regularly and automatically performed, and wherein displaying the real position, determining, computing, detecting the spatial position, constructing and displaying steps are performed using the last obtained image data of the imaged zone.

3. The method of claim 1, wherein the localizing system is a magnetic tracking system based on magnetic detection and the imaging system is based on X-ray Computed Tomography.

4. The method of claim 3, wherein the reference marker comprises:

a magnetic element having at least two coils arranged in a manner to define at least two vectors in the coordinate system of the magnetic tracking system; and a geometric element comprising components visible on image data of the imaging system and having a unique geometry detectable by the imaging system.

5. The method of claim 4, wherein the at least two coils are coils arranged in a different manner with respect to one another, and the components are of different shapes and/or arranged in a different manner with respect to one another.

* * * * *